United States Patent [19]

Salz et al.

[11] Patent Number: 5,698,020
[45] Date of Patent: Dec. 16, 1997

[54] PHOTOCHROMIC DENTAL MATERIAL

[75] Inventors: Ulrich Salz, Lindau, Germany; Peter Burtscher, Nuetziders, Austria; Volker Rheinberger, Vaduz, Liechtenstein; Heinz Durr, Saarbrucken, Germany

[73] Assignee: Ivoclar AG, Liechtenstein

[21] Appl. No.: 648,810

[22] Filed: May 16, 1996

[30] Foreign Application Priority Data

May 26, 1995 [DE] Germany ............... 19520016.0

[51] Int. Cl.$^6$ ............... A61K 6/02; C09K 9/00; C09B 57/00; C07D 471/04
[52] U.S. Cl. ............... 106/35; 501/13; 523/116; 523/118; 433/228.1
[58] Field of Search ............... 106/35; 501/13; 523/116, 118; 433/278.1

[56] References Cited

U.S. PATENT DOCUMENTS

| | | | |
|---|---|---|---|
| 3,208,860 | 9/1965 | Amistead et al. | 501/13 |
| 4,046,781 | 9/1977 | Yu | 260/347.7 |
| 4,600,389 | 7/1986 | Schwartz | 106/35 |
| 4,891,336 | 1/1990 | Prassas | 501/13 |
| 4,979,976 | 12/1990 | Havens et al. | 501/13 |
| 5,162,130 | 11/1992 | McLaughlin | 433/203.1 |

FOREIGN PATENT DOCUMENTS

| | | |
|---|---|---|
| 0 389 239 | 9/1990 | European Pat. Off. . |
| 0 422 514 A1 | 4/1991 | European Pat. Off. . |
| 29 06 193 C2 | 8/1980 | Germany . |
| 30 36 103 C2 | 7/1981 | Germany . |
| 32 47 800 C2 | 7/1983 | Germany . |
| 32 20 257 C2 | 12/1983 | Germany . |
| 37 17 762 C2 | 3/1987 | Germany . |
| 39 39 998 A1 | 6/1991 | Germany . |
| 40 29 230 A1 | 3/1992 | Germany . |
| 41 10 611 A1 | 5/1992 | Germany . |
| 2 190 917 | 12/1987 | United Kingdom . |
| 2 230 271 | 10/1990 | United Kingdom . |

OTHER PUBLICATIONS

Trotter, "Photochrome und photosensitive Güaser," *Spektrum der Wissenschaft*, Jun. 1991.

Dürr, "Perspektiven auf dem Gebiet der Photochromie: 1,5-Elektrocycliserung von heteroanalogen Pentadienty-Anionen als Basis eines neuartigen Systems," *Angew. Chem.*, 101:427–445 (1989).

*Primary Examiner*—Melissa Bonner
*Attorney, Agent, or Firm*—Nixon, Hargrave, Devans & Doyle

[57] ABSTRACT

The invention relates to dental materials which contain a photochromic material such as for example a photochromic dye, a photochromic glass, a photochromic ceramic and/or a photochromic glass ceramic and which can be visually distinguished from natural tooth material after irradiating with light, but which assume their original colour again after a certain period has expired.

14 Claims, No Drawings

PHOTOCHROMIC DENTAL MATERIAL

The invention relates to dental materials which contain a photochromic material such as for example a photochromic dye, a photochromic glass, a photochromic ceramic and/or a photochromic glass ceramic and which can be visually distinguished from the natural tooth material following irradiation with light.

In restorative dentistry, tooth-coloured restoration materials are being used to an increasing extent on aesthetic grounds. These materials have the disadvantage that they can be visually distinguished from the natural tooth substance only with difficulty, with the result that the removal of excess material and the working and fitting of, for example, fillings becomes more difficult. This results in healthy tooth substance frequently being removed unnecessarily or, on the other hand, surplus dental material being missed which then, as a retention niche, can encourage the formation of plaque and lead to parodontal problems. Also, when tooth-coloured fillings are being removed, the poor visibility of the transition from filling to tooth substance frequently causes either too much healthy tooth substance to be removed or remains of filling to be overlooked.

Similar problems arise when tooth-coloured fixing materials are used for cementing tooth-coloured restorations.

U.S. Pat. No. 5,162,130 discloses dental materials which contain a photosensitive material. These dental materials permit the production of dental restorations which can be matched in terms of colour to their environment by irradiation with UV light and subsequent heating. Since the colour of the restorations is permanently changed by the irradiation and heating, the photosensitive materials are not suitable for the temporary visualization of colourless or tooth-coloured dental materials.

Dental materials are known from U.S. Pat. No. 4,600,389 which contain fluorescent lanthanide compounds which display a reddish or greenish fluorescence when irradiated with a mercury-vapour lamp and thus permit a differentiation between dental material and tooth substance.

GB 2 190 917 discloses a coloured or fluorescent coating material for teeth which forms a removable protective film.

DE 39 39 998 A1 relates to a process for the optical differentiation between dental material and natural tooth material which is based on the use of a fluorescent substance and special light filters.

GB 2 230 271 A discloses a dental material which contains a dye which can be excited to fluorescence by visible light.

Fluorescent dental materials have the disadvantage that the florescence only occurs upon simultaneous irradiation with a suitable light source, so that, alongside the dentist's usual tools, a light guide must also be accommodated in the oral cavity, as a result of which the dentist's work in the narrow oral cavity is made more difficult. The use of special lamps is also frequently necessary. Moreover, the natural tooth substance has a strong fluorescence of its own, so that relatively high concentrations of the fluorescent dye are needed in the dental material in order to ensure a good distinguishability of dental material and tooth substance. This results in a clearly visible change in colour of the dental material, caused by the fluorescent dye, particularly in the case of fluorescent dyes having an absorption maximum above 400 nm.

It is the object of the present invention to provide a dental material, the colour of which can be altered by short-time irradiation with a suitable light source in such a way that a problem-free visual differentiation of the dental material from the natural tooth substance is ensured, and which assumes its original colour again after a period of time sufficient to remove surplus dental material or to work the dental material.

This object is achieved by dental materials which additionally contain a photochromic material, such as for example a photochromic dye, a photochromic glass, a photochromic ceramic and/or a photochromic glass ceramic.

Photochromism is understood to be a reversible transition of a chemical substance between two states with different absorption spectra, the transition being caused at least in one direction by electromagnetic radiation.

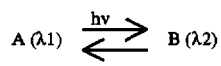

When irradiated with light in the wavelength range of the absorption maximum λ1 of the starting state A, the substance changes to the higher-energy intensively coloured form B. The reverse reaction from B to A proceeds in most cases spontaneously and, compared with the forward reaction, at a slower speed.

Preferred photochromic materials are photochromic dyes and photochromic glasses as well as photochromic ceramics or glass ceramics.

Suitable photochromic dyes are described for example in *Photochromism—Molecules and Systems* (Dürr, H.; Bouas-Laurent, H., Publisher, Elsevier, 1990). Preferred photochromic dye systems are based on the cis/trans isomerism of azobenzene compounds or stilbenes, on the interconversion or electrocyclic ring-closure/ring-opening reaction of spiropyran systems or spirooxazins to merocyanins, or on the 1,5-electrocyclization of pentadienyl anions.

A preferred group of photochromic dyes are spiro[1,8a-indolizine] derivatives, in particular spiro[1,8a-dihydroindolizine]- and spiro[1,8a-tetrahydroindolizine] derivatives. Suitable derivatives and processes for their production are disclosed for example in DE 29 06 193 C2 and DE 32 20 257 C2.

Systems which are based on a 1,5-electrocyclization, as described by H. Dürr in *Angew. Chem.* 101 (1989), pages 427 to 445 in Chapter 3, are particularly preferred.

Quite particularly preferred are spiro[fluorene-9,1'[1,8a] dihydroindolizine] derivatives, in particular derivatives according to the formula

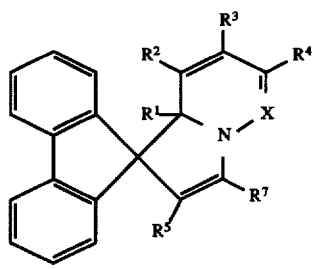

in which

X is C—R$^5$ or N;

R$^1$ is H or CH$_3$;

R$^2$ is H, CH$_2$=C(CH$_3$)—COO— or, together with R$^3$, a fused benzene ring (—(CH$_2$=CH$_2$—)$_2$);

R$^3$ is H, CH$_3$, COOCH$_3$, CN, CH$_2$=C(CH$_3$)—COO— or, together with R$^2$, a fused benzene ring (—(CH$_2$=CH$_2$—)$_2$);

R$^4$ is H or CH$_3$;

$R^5$ is H or $CH_2=C(CH_3)$—COO—;

$R^6$ is $COOCH_3$ or $COCH_3$ and $R^7$ is $COOCH_3$ or $COCH_3$.

Preferred substituents are X=N; $R^1$=H; $R^2$=H; $R^3$=H; $R^4$=H or $CH_3$; $R^6$=$COOCH_3$; $R^7$=$COOCH_3$.

Quite particularly preferred systems are X=N, $R^1$=$R^2$=$R^3$=H; $R^4$=$CH_3$; $R^6$=$R^7$=$COOCH_3$ (1'-H-2',3'-dicarbomethoxy-5'methyl-spiro[fluorene-9,1'-pyrrolo-[1,2-B]-pyridazine]); X=N, $R^1$=$R^2$=$R^3$=$R^4$=H; $R^6$=$R^7$=$COOCH_3$; X=N, $R^1$=$CH_3$, $R^2$=$R^3$=H, $R^4$=$CH_3$; $R^6$=$R^7$=$COOCH_3$; and X=N, $R^1$=$R^2$=$R^3$=$R^4$=H; $R^6$=$COCH_3$, $R^7$=$COOCH_3$.

The change in colour of the dyes preferred according to the invention is to be attributed to the betaine II (state B) which forms upon irradiation:

(for example inlays, onlays and crowns). Here, it is frequently desired that the photochromic cement used for the cementing changes colour only during the cementation, but is permanently colourless or tooth-coloured following cementation, in order to avoid the cement changing colour for example by insolation, particularly in the front teeth region.

The aforementioned spiro[1,8a-indolizine] derivatives are particularly suitable for producing irreversibly decolorizable dental materials, since they are frequently destroyed during radical polymerization of the dental material, which results in a non-reversible decolorization. This property also permits a selective decolorization of the dental material after the dental restoration is finished.

Since, in the case of irreversibly decolorizable dental materials, hardening of the material is associated with a

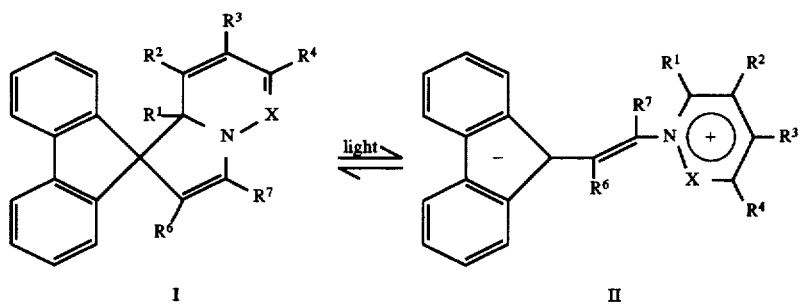

I    II

Photochromic dyes are preferably used in a quantity of 0.0001 to 0.1% by wt., particularly preferably 0.002 to 0.01% by wt., relative to the total weight of dental material. Preferred according to the invention are those dyes whose absorption maximum λ1 of the state A lies in the wavelength range of standard commercial polymerization lamps for dental composites, preferably in the range from 400 to 500 nm. The absorption maximum λ2 of the activated state B lies in the visible wavelength range, so that the dental material appears coloured after irradiation and can easily be visually distinguished from the natural tooth substance.

For the production of photo-hardenable dental materials, those dyes are also preferred which require an irradiation time for producing the coloured state B which is less than the time required for triggering polymerization, so that the dental material can be coloured by a short irradiation and surplus material can be removed in the still unhardened but coloured state. Photochromic materials which require a radiation time of at most 1 to 3 seconds for producing the coloured state B are thus particularly preferred.

For the initial hardening, the dental material is irradiated again, e.g. for 10 seconds, the hardened material remaining coloured and thus readily recognizable. The dental material is then coloured; for the final hardening, it is again decolorized. In principle, however, it is also possible to harden the dental material immediately by a single longer irradiation.

Self-hardening dental materials usually require several minutes to harden, normally about 2 to 4 minutes. Here, too, photochromic materials which require an irradiation time of at most 1 to 3 seconds to produce the coloured state are preferred, so that surplus material can be removed in the unhardened state.

The photochromic dyes according to the invention are suitable for producing both reversible and irreversible decolorizable dental materials.

Irreversibly decolorizable dental materials are suitable in particular for cementing tooth-coloured ceramic restorations partial decolorization of the material because the photochromic dye is destroyed, hardening in two stages is recommended in these cases.

After the first short-term irradiation of the dental material to produce the coloured state and optionally after removing or working the unhardened dental material, it is irradiated a second time for superficial hardening. In most cases, an irradiation time of about 10 seconds is sufficient for this purpose. If necessary, the hardened but still coloured dental material surpluses can then be removed. The dental material is then completely hardened by a relatively .long irradiation of preferably 40 to 60 seconds, considerable decolorization taking place.

Complete decolorization of the material takes place by the subsequent reverse reaction of non-destroyed dye molecules to the starting state A and, if necessary, by removing the surface layer of the material. In the surface layer, radical polymerization is frequently inhibited by oxygen which diffuses in, so that polymerization and thus destruction of the photochromic dye is incomplete in this layer. In practice, this layer, which is usually about 100 µm thick, is removed upon polishing of the fillings and cement edges.

The time taken for complete decolorization of the material depends on the type and the quantity of dye used. In the case of the dyes preferred according to the invention, the material is already completely decolorized during the 40–60 second irradiation in the case of a dye content of about 0.002% by wt., whilst for a dye content of about 0.01% by wt. complete decolorization takes place within 24 hours with the exclusion of light after irradiation for 40 to 60 seconds.

Permanently reversible photochromic dental materials are obtained with the combination of organic photochromic dyes with heat-hardening composites when the dental material is hardened in the uncolored state. In the case of photochromic dyes preferred according to the invention, whose photochromism is based on a 1,5-electrocyclization, this is presumably to be attributed to the fact that the dyes are accessible only in the open-chained coloured form to the radical destruction. Heat-hardening dental materials are suitable particularly for producing inlays and onlays.

Permanently reversible photochromic dental materials based on organic photochromic dyes can also be produced with self- or cold-hardening and dual-hardenable systems. In the case of a self- or cold-hardening system, an amine-containing base paste is mixed with a peroxide-containing catalyst paste. The radical polymerization is initiated by the reaction of amine and peroxide. Dibenzoyl peroxide is the preferred catalyst.

In the case of dual-hardenable systems, the base paste additionally contains a photoinitiator, such as for example camphor quinone, so that the base paste can be used either on its own as a light-hardening dental material or together with the catalyst paste as a light- and self-hardening dental material.

In the case of self- and dual-hardening systems, the reversibility of the colour change is dependent on the ratio of catalyst to photochromic dye. When using the preferred catalyst dibenzoyl peroxide and a usual catalyst concentration of for example about 0.75% by wt. dibenzoyl peroxide (50%), a dye concentration of 0.01 to 0.1% by wt. is preferred. Even in the case of self- and dual-hardening systems, reversible photochromism is only achieved when hardening of the dental material takes place in the uncoloured state.

In the case of the preferred photochromic dyes, the decolorizing time for reversibly photochromic dental materials both in the case of heat- and also of self- and dual-hardening systems is about 2 hours, preferably about 1 hour. However, since the working of the dental material and removal of surplus dental material usually takes place in the light of an operating lamp (wavelength range about 400–700 nm), no decolorization normally takes place during working, so that photochromic materials with a clearly lower decolorization time are also suitable according to the invention.

Photochromic glasses suitable according to the invention are for example disclosed in U.S. Pat. No. 4,891,336, U.S. Pat. No. 4,979,976 and EP 0 422 514 A1. These are photochromic glasses based on metal halides. Silicon-aluminium-borate glasses, whose photochromic effect is based on the interaction of silver, chlorine, bromine and copper, in each case in several different oxidation stages, are particularly suitable. Particularly preferred glasses are described in DE 30 36 103 C 2, U.S. Pat. No. 3,208,860 and in U.S. Pat. No. 4,046,781. Quite particularly preferred are glasses with the composition:

| Constituent | % by wt. |
| --- | --- |
| $SiO_2$ | 48.0–60.0 |
| $Al_2O_3$ | 5.0–12.0 |
| $B_2O_3$ | 16.0–25.0 |
| $Li_2O$ | 1.6–3.5 |
| $Na_2O$ | 3.0–7.0 |
| $K_2O$ | 5.0–10.0 |
| $TiO_2$ | 1.8–2.2 |
| $ZrO_2$ | 4.0–6.0 |
| Ag | 0.15–0.5 |
| CuO | 0.005–0.02 |
| Cl | 0.15–0.25 |
| Br | 0.05–0.15 |

Such glasses are for example marketed by Deutsche Spezialglas AG under the name "Photosolar Supergrey D-1426".

Dental materials based on metal halide-containing glasses, ceramics or glass ceramics turn dark when irradiated with light. In general, they react sensitively to the whole spectrum of visible light, without showing a particularly marked absorption maximum. An irradiation time of 20 to 40 seconds is generally sufficient to make the dental material clearly visible.

The colour of the photochromic glasses on exposure to light is based on the reduction of ionic silver (state A) to elementary silver (state B), which is again oxidized under the exclusion of light with simultaneous decolorization. Complete decolorization preferably takes place within 0.5 to 1.5 hours.

As a rule, dental materials based on photochromic glasses, ceramics or glass ceramics display a permanent reversibility of the photochromism, and they do not lose their ability for photochromism even when the dental material containing them, such as for example a filling material, is subjected over a relatively long period of time to the chemical and physical influences which affect natural teeth. On aesthetic grounds these materials are therefore preferably suitable for use in the side tooth region or as underfilling materials.

Photochromic glasses, ceramics and/or glass ceramics are preferably used as fillers, preferably in a concentration of 10 to 90% by wt., particularly preferably 30 to 60% by wt. relative to the total weight of the dental material. Glasses in powder form having an average grain size of 0.7 to 20 µm, in particular 0.7 to 5 µm and glasses with a refractive index of 1.50 to 1.58 are preferred for use in dental materials. The choice of polymerization catalyst does not have an effect on the photochromism of the glasses, ceramics and glass ceramics.

The photochromic materials according to the invention are compatible with very different dental materials and prove advantageous particularly when incorporated into colourless or tooth-coloured dental materials, since they essentially lead to no visible change in the colour of the material.

Dental materials within the meaning of the invention are in particular composite filling materials, securing plastics for inlays, onlays, crowns and bridges and block-out materials.

Dental materials based on a polymerizable, ethylenically unsaturated monomer as binding agent, a catalyst for the hot, cold and/or photopolymerization and 20 to 90% by wt. of an inorganic filler are preferred.

Suitable as polymerizable organic binding agents are all binding agents which can be used for a dental material, in particular monofunctional or polyfunctional methacrylates which can be used alone or in mixtures. Coming into consideration as examples of these compounds are methyl methacrylate, isobutyl methacrylate, cyclohexyl methacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol-A dimethacrylate, trimethylolpropane trimethacrylate, 2,2-bis-4-(3-methacryloxy-2-hydroxypropoxy)-phenyl propane (bis-GMA) and the reaction products of isocyanates, in particular di- and/or triisocyanates and OH group-containing methacrylates. Examples of these are the reaction products of 1 mol hexamethylene diisocyanate with 2 mol 2-hydroxyethylene methacrylate, of 1 mol tri-(6-isocyanatohexyl) biuret with 3 mol 2-hydroxyethyl methacrylate and (6-isocyanatohexyl) biuret with 3 mol 2-hydroxyethyl methacrylate and of 1 mol 2,2,4-trimethyl hexamethylene diisocyanate with 2 mol 2-hydroxyethyl methacrylate.

Preferred as catalysts for the heat-hardening systems are peroxides, in particular dibenzoyl peroxide, dilauroyl peroxide, tert.-butyl peroctate and tert.-butyl perbenzoate. 2,2'-azoisobutyric acid nitrile (AIBN), benzpinacol and 2,2'-dialkyl benzpinacols are also suitable.

Used as catalysts for the cold polymerization are radical-supplying systems, for example benzoyl or lauroyl peroxide together with amines such as N,N-dimethyl-p-toluidine, N,N-dihydroxyethyl-p-toluidine or other structurally related amines.

Usable as initiators for the photopolymerization are for example benzophenone and its derivatives and benzoin and its derivatives. Other preferred photoinitiators are the α-diketones such as 9,10-phenanthrene quinone, diacetyl, furil, anisil, 4,4'-dichlorobenzil and 4,4'-dialkoxy benzil. Camphor quinone is particularly preferably used.

Combinations of cold and photocatalysts are suitable as catalysts for dual-hardenable systems. The use of camphor quinone and dibenzoyl peroxide in combination with the aforementioned amines is preferred.

Used as inorganic fillers are e.g. quartz, glass ceramic or glass powders, the oxides of aluminium or silicon, barium silicate glasses and Li/Al silicate glasses, barium glasses, very finely divided silicas, in particular pyrogenic or precipitated silicas.

Suitable fillers are for example disclosed in DE-OS 40 29 230. Fillers of type (A) are described in DE-PS 32 47 800.

The photochromic glasses according to the invention are preferably used as component (B), either alone or in combination with a barium silicate glass which has the required parameters.

The invention is described in more detail below with reference to examples.

EXAMPLE 1

Photochromic, Light-Hardening Tooth-Coloured Composite Cement

A base paste having the following composition is produced by mixing the components (analogous to DE 40 29 230 A1):

| Component | % by wt. |
|---|---|
| Ba—Al silicate glass, silanized | 40.0 |
| Ytterbium trifluoride | 25.0 |
| Spheroidal mixed oxide, silanized* | 10.0 |
| Bisphenol-A glycidyl dimethacrylate (bis-GMA) | 12.28 |
| Triethylene glycol dimethacrylate (TEGDMA) | 6.22 |
| Urethane dimethacrylate (UDMA)** | 6.22 |
| Camphor quinone | 0.07 |
| Cyanoethyl methylaniline | 0.07 |
| N,N-diethyl-3,5-di-tert.-butylaniline | 0.1 |
| 3,5-di-tert.-butyl-4-hydroxytoluene (BHT) | 0.03 |
| HD 579 | 0.01 |

*Filler A according to DE 40 29 230 A1
**Reaction product of 1 mol trimethylhexamethylene diisocyanate and 2 mol hydroxyethyl methacrylate N,N-diethyl-3,5-di-tert.-butylaniline, BHT and, as fillers, silanized Ba-Al-silicate glass, ytterbium trifluoride and spheroidal mixed oxide are incorporated into a monomer mixture of bis-GMA, TEGDMA, UDMA, camphor quinone and cyanoethyl methylaniline. 0.01% by wt. of the photochromic dye HD 579 (Table 1) are also added.

A catalyst paste having the following composition is also produced (analogous to DE 40 29 230 A1):

| Component | % by wt. |
|---|---|
| Ba—Al silicate glass, silanized | 40.0 |
| Ytterbium trifluoride | 25.0 |
| Spheroidal mixed oxide, silanized | 10.0 |
| Bis-GMA | 12.22 |
| TEGDMA | 6.0 |
| UDMA | 6.0 |
| Benzoyl peroxide (50%) | 0.75 |
| BHT | 0.03 |

Into a monomer mixture of bis-GMA, TEGDMA, UDMA, BHT and 50% benzoyl peroxide are incorporated, as fillers, silanized Ba-Al silicate glass, ytterbium trifluoride and spheroidal mixed oxide.

The pastes are mixed in the ratio 1:1 and inserted with the part to be cemented (crown, bridge, veneer, inlay, onlay). The cement emerging from the cementing crevice is irradiated for 1 to 3 seconds with a standard commercial polymerization lamp (Heliolux® GTE, Vivadent) at a wavelength of 400 to 500 nm. The cement suddenly turns an intense red, but remains thinly viscous. In this phase the coarsest surpluses can easily be removed.

After irradiating further for about 20 seconds, the cement polymerizes to a hard material which is also red in colour. The polymerized-out surpluses remain easily visible and can be removed with precision.

By irradiating for a further 40 to 60 seconds the cement is almost completely decolorized. The remaining slight pink colour disappears after storage without irradiation within 24 hours. The hardened material has a tooth-coloured appearance. The decolorization is irreversible since the dye used is destroyed by the radical polymerization.

EXAMPLES 2 to 10

A base paste is produced according to Example 1, but using the dyes given in Table 1 as photochromic materials. The base pastes are mixed with the catalyst paste according to Example 1 and irradiated as described in Example 1. The dental materials display different colours (Table 1) and colour intensities, depending on the dye chosen. Decolorization is irreversible in all cases.

EXAMPLE 11

Photochromic Filling Material

A material having the following composition is produced by mixing the components:

| Components | % by wt. |
|---|---|
| Photosolar supergrey D-1426* | 15.0 |
| Ba—Al silicate glass, silanized | 35.0 |
| Ytterbium trifluoride | 15.0 |
| Spheroidal mixed oxide, silanized | 15.0 |
| Aerosil OX-50,** silanized | 1.0 |
| Bis-GMA | 8.0 |
| TEGDMA | 3.8 |
| UDMA | 7.02 |
| Monomethyl hydroquinone (MeHQ) | 0.02 |
| Camphor quinone | 0.06 |
| Cyanoethyl methylaniline | 0.1 |

*Photochromic glass from Deutsche Spezial Glas AG, the glass is ground to an average grain size of 0.7 to 5 µm
**Aerosil OX-50 (Degussa AG)

The material is introduced into a cavity like a usual filling material and irradiated for 40 to 60 seconds with a polymerization lamp (Heliolux GTE, Vivadent) with a wavelength of 400 to 500 nm. Upon irradiating the paste, the composite hardens and immediately turns grey. Within 1.5 hours' storage with the exclusion of light, the testpiece has again lost its colour and has a tooth-coloured appearance. When the testpiece is irradiated again (about 10 seconds), it once again turns grey and, after storage with the exclusion of light, decolorization again takes place. This process can be repeated as often as desired.

TABLE 1

Derivatives of compound I

| Example | Dye | X | $R^1$ | $R^2$ | $R^3$ | $R^4$ | $R^5$ | $R^6$ | $R^7$ | Colour |
|---|---|---|---|---|---|---|---|---|---|---|
| 1 | HD 579 N | H | H | H | H | $CH_3$ | — | $COOCH_3$ | $COOCH_3$ | red |
| 2 | HD 578 N | H | H | H | H | H | — | $COOCH_3$ | $COOCH_3$ | red |
| 3 | HD 580 N | H | H | $COOCH_3$ | H | H | — | $COOCH_3$ | $COOCH_3$ | red |
| 4 | HD 581 N | H | H | H | CN | H | — | $COOCH_3$ | $COOCH_3$ | red |
| 5 | HD 582 N | H | $CH_3$ | H | H | $CH_3$ | — | $COOCH_3$ | $COOCH_3$ | green |
| 6 | HD 604 N | H | | —(CH$_2$=CH$_2$)$_2$— | | H | — | $COCH_3$ | $COCH_3$ | blue-violet |
| 7 | HD 606 N | H | H | H | H | H | — | $COCH_3$ | $COOCH_3$ | |
| 8 | HD 607 C-$R^5$ | H | $CH_2$=C—(CH$_3$)—COO— | H | H | H | $COOCH_3$ | $COOCH_3$ | green |
| 9 | HD 608 C-$R^5$ | H | H | H | H | $CH_2$=C(CH$_3$)—COO— | $COOCH_3$ | $COOCH_3$ | green |
| 10 | HD 609 C-$R^5$ | H | H | $CH_2$=C(CH$_3$)—COO— | H | H | $COOCH_3$ | $COOCH_3$ | green |

We claim:
1. Dental material, characterized in that it contains a photochromic dye.
2. Dental material according to claim 1, characterized in that it contains, as photochromic dye, at least one photochromic spiro[1,8a-indolizine] derivative.
3. Dental material according to claim 2, characterized in that it contains at least one spiro[1,8a-dihydroindolizine] and/or spiro[1,8a-tetrahydroindolizine] derivative.
4. Dental material according to claim 3, characterized in that it contains at least one spiro[fluorene-9,1'[1,8a]-dihydroindolizine] derivative.
5. Dental material according to claim 4, characterized in that it contains at least one spiro[fluorene-9,1'[1,8a]-dihydroindolizine] derivative according to the formula

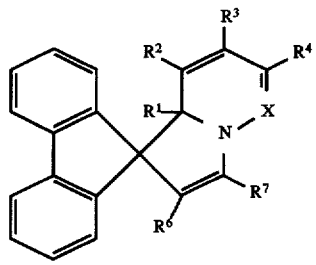

in which
X is C—$R^5$ or N;
$R^1$ is H or $CH_3$;
$R^2$ is H, $CH_2$=C(CH$_3$)—COO— or, together with $R^3$, a fused benzene ring (—(CH$_2$=CH$_2$—)$_2$);
$R^3$ is H, $CH_3$, $COOCH_3$, CN, $CH_2$=C(CH$_3$)—COO— or, together with $R^2$, a fused benzene ring (—(CH$_2$=CH$_2$—)$_2$);
$R^4$ is H or $CH_3$;
$R^5$ is H or $CH_2$=C(CH$_3$)—COO—;
$R^6$ is $COOCH_3$ or $COCH_3$ and $R^7$ is $COOCH_3$ or $COCH_3$.

6. Dental material according to claim 1, characterized in that it additionally contains an ethylenically unsaturated monomer, a catalyst for the hot, cold and/or photopolymerization and 20 to 90% by wt. of an inorganic filler.

7. Dental material, characterized in that it contains a photochromic glass which comprises the components

| | |
|---|---|
| $SiO_2$ | 48.0–60.0 % by wt. |
| $Al_2O_3$ | 5.0–12.0 % by wt. |
| $B_2O_3$ | 16.0–25.0 % by wt. |
| $Li_2O$ | 1.6–3.5 % by wt. |
| $Na_2O$ | 3.0–7.0 % by wt. |
| $K_2O$ | 5.0–10.0 % by wt. |
| $TiO_2$ | 1.8–2.2 % by wt. |
| $ZrO_2$ | 4.0–6.0 % by wt. |
| Ag | 0.15–0.5 % by wt. |
| CuO | 0.005–0.02 % by wt. |
| Cl | 0.15–0.25 % by wt. |
| Br | 0.05–0.15 % by wt. |

8. Dental material according to claim 7, wherein the dental material is selected from the group consisting of composite filling materials, securing plastics for inlays, onlays, crowns and bridges and block out materials.
9. Dental material according to claim 7, characterized in that it additionally contains an ethylenically unsaturated monomer, a catalyst for the hot, cold and/or photopolymerization and 20 to 90% by wt. of an inorganic filler.
10. Dental material comprising a polymerizable material and a photochromic material.
11. Dental material according to claim 10, wherein the photochromic material is selected from the group consisting of a photochromic glass, a photochromic ceramic, a photochromic glass ceramic, and combinations thereof.
12. Dental material according to claim 10, wherein the dental material is selected from the group consisting of composite filling materials, securing plastics for inlays, onlays, crowns and bridges and block out materials.
13. Dental material according to claim 10, wherein the polymerizable material is an ethylenically unsaturated monomer and wherein said dental material further comprises a catalyst for the hot, cold and/or photopolymerization and 20 to 90% by wt. of an inorganic filler.
14. Dental material according to claim 1, wherein the dental material is selected from the group consisting of composite filling materials, securing plastics for inlays, onlays, crowns and bridges and block out materials.

* * * * *